United States Patent [19]

Greff et al.

[11] Patent Number: 5,580,568
[45] Date of Patent: Dec. 3, 1996

[54] CELLULOSE DIACETATE COMPOSITIONS FOR USE IN EMBOLIZING BLOOD VESSELS

[75] Inventors: Richard J. Greff, Yorba Linda; Michael L. Jones, Capistrano Beach; Scott Evans, Santa Ana, all of Calif.

[73] Assignee: Micro Therapeutics, Inc., San Clemente, Calif.

[21] Appl. No.: 508,248

[22] Filed: Jul. 27, 1995

[51] Int. Cl.$^6$ .......................... A61K 49/00; G01N 31/00; G01N 33/48

[52] U.S. Cl. .......................... 424/423; 424/9.3; 424/9.322; 424/9.35; 514/57

[58] Field of Search .......................... 424/423, 9.3, 9.322, 424/9.35; 514/57

[56] References Cited

U.S. PATENT DOCUMENTS

| | | |
|---|---|---|
| 4,079,124 | 3/1978 | Winchell. |
| 4,631,188 | 12/1986 | Stoy et al.. |
| 4,795,741 | 1/1989 | Leshchiner et al.. |
| 4,938,763 | 7/1990 | Dunn et al.. |
| 5,202,352 | 4/1993 | Okada et al. .......................... 514/475 |
| 5,443,454 | 8/1995 | Tanabe et al.. |
| B1 4,938,763 | 7/1995 | Dunn et al.. |

FOREIGN PATENT DOCUMENTS

| | | |
|---|---|---|
| 5-57014 | 3/1993 | Japan. |
| 5-253283 | 10/1993 | Japan. |
| 6-107549 | 4/1994 | Japan. |

OTHER PUBLICATIONS

Casarett and Doull's Toxicology, Amdur et al., Editors, *Toxic Effects of Metals*, 4th Edition, pp. 661–664, Pergamon Press, New York, New York.

Guglielmi, et al., *Electrothrombosis of Saccular Aneurysms via Endovascular Approach*, J. Neurosurg., 78:9–14 (1991).

Kinugasa, et al., *Early Treatment of Subarachnoid Hemorrhage After Preventing Rerupture of an Aneurysm*, J. Neurosurg., 83:34–41 (1995).

Kinugasa, et al., *Prophylatic Thrombosis to Prevent New Bleeding and to Delay Aneurysm Surgery*, Neurosurgery, 36(4):661–667 (1995).

Kinugasa, et al., *Direct Thrombosis of a Pseudoaneurysm after Obliteration of a Carotid–Cavernous Fistula with Cellulose Acetate Polymer: Technical Case Report*, Neurosurgery, 35(4):755–760 (1994).

Kinugasa, et al., *Direct Thrombosis of Aneurysms with Cellulose Acetate Polymer, Part II: Preliminary Clinical Experience*, J. Neurosurg., 77:501–507 (1992).

Mandai, et al., *Direct Thrombosis of Aneurysms with Cellulose Acetate Polymer, Part I: Results on Thrombosis in Experimental Aneurysms*, J. Neurosurg., 77497–500 (1992).

Miyatake, et al., *Cobb's Syndrome and its Treatment with Embolization*, J. Neurosurg., 72:497–499 (1990).

Naitoh, et al., *Removal of Beta–2 Microglobulin by Diffusion Alone is Feasible Using Highly Permeable Dialysis Membranes*, Trans Am. Soc. Artif. Intern. Organs, 630–634 (1988).

Sadato, et al., *Experimental Study and Clinical Use of Poly(vinyl acetate) Emulsion as Liquid Embolisation Material*, Neuroradiology, 36:634–641 (1994).

Sugiu, et al., *Direct Thrombosis of Experimental Aneurysms with Cellulose Acetate Polymer (CAP): Technical Aspects, Angiographic Follow Up, and Histological Study*, J. Neurosurg., 83:531–538 (1995).

Taki, et al., *A New Liquid Material for Embolization of Arteriovenous Malformations*, Am. J. Neuroradiology, 11:163–168 (1990).

Taki, et al., *Selection and Combination of Various Endovascular Techniques in the Treatment of Giant Aneurysms*, J. Neurosurg., 77:37–42 (1992).

Taki, et al., *Possibility and Limit of Intravascular Surgery*, Medical Tribune, pp. 46–47 (1989).

Terada, et al., *Embolization of Arteriovenous Malformations with Peripheral Aneurysms using Ethylene Vinyl Alcohol Copolymer*, J. Neurosurg., 75:655–660 (1991).

Yamashita, et al, *Characteristics of Ethylene Vinyl Alcohol Copolymer (EVAL) Mixtures*, Am. J. Neuroradiology, 15:1103–1105 (1994).

*Primary Examiner*—Nathan M. Nutter
*Attorney, Agent, or Firm*—Burns, Doane, Swecker & Mathis, LLP

[57] ABSTRACT

Disclosed are compositions suitable for use in embolizing blood vessels which compositions comprise a cellulose diacetate polymer, a biocompatible solvent and a water insoluble contrasting agent selected from the group consisting of tantalum, tantalum oxide and barium sulfate. Also disclosed are methods for embolizing a blood vessel using the compositions described herein.

15 Claims, No Drawings

CELLULOSE DIACETATE COMPOSITIONS FOR USE IN EMBOLIZING BLOOD VESSELS

BACKGROUND OF THE INVENTION

1. Field of the Invention

This invention is directed to compositions suitable for use in embolizing blood vessels. In particular, this invention is directed to embolizing compositions comprising cellulose diacetate, a biocompatible solvent and a water insoluble contrasting agent. The compositions of this invention find particular utility in embolizing blood vessels in, for example, the treatment of aneurysms and in ablating diseased tissues.

2. References

The following publications are cited in this application as superscript numbers:

[1] Mandai, et al., "Direct Thrombosis of Aneurysms with Cellulose Acetate Polymer", *J. Neurosurg.*, 77:497–500 (1992)

[2] Kinugasa, et al., "Direct Thrombosis of Aneurysms with Cellulose Acetate Polymer", *J. Neurosurg.*, 77:501–507 (1992)

[3] Naitoh, et al., "Removal of Beta-2-Microglobulin by Diffusion Alone is Feasible Using Highly Permeable Dialysis Membranes", *Trans Am. Soc. Artifi Intern. Organs*, 630–634 (1988)

[4] Casarett and Doull's *Toxicology*, Amdur et al., Editors, Pergamon Press, New York, pp. 661–664 (1975)

All of the above references are herein incorporated by reference in their entirety to the same extent as if each individual reference was specifically and individually indicated to be incorporated herein by reference in its entirety.

State of the Art

It is desirable in many clinical situations to embolize blood vessels to prevent/control bleeding (e.g., organ bleeding, gastrointestinal bleeding, vascular bleeding, bleeding associated with an aneurysm) or to ablate diseased tissue (e.g., tumors, etc.). Embolization of blood vessels has heretofore employed polymer compositions and particulates, e.g., silicone, metallic coils, sclerosing materials and the like. Polymeric materials employed in the polymer compositions include those which polymerize in situ at the vascular site (e.g., cyanoacrylates) and those wherein a preformed polymer in situ precipitates from a carrier solution at the vascular site.

The in situ polymerization of cyanoacrylates delivered via a catheter causes complications due to premature polymerization and/or adhesion of the polymer to the catheter. Accordingly, there has been recent focus on incorporating preformed polymeric materials into embolization compositions. Ideally, such compositions should be easy to deliver (e.g., low viscosity) and should cause rapid embolization in the intended vascular site. Additionally, these compositions should be sterile, stable, biocompatible and radiopaque. This last property is necessary in order to monitor injection of the embolizing composition into the vascular site and to confirm its presence after the procedure is complete.

Current embolizing compositions employing preformed polymers typically fail to meet one or more of the requirements of ideal embolizing compositions and a compromise must be made in selecting the embolizing agents relative to the given clinical case. At times, embolization of the blood vessel, although called for by the clinical condition of the patient, is not performed due to difficulties in selecting an embolizing composition suitable for use in the given case.

Failure of such embolizing compositions to meet these ideal requirements often arises from the particular combination of embolizing and contrast agents used in the embolizing composition. Specifically, the biocompatible embolizing agent should produce a well defined coherent plug/solid upon contact with blood and the contrast agent should be encapsulated in the formed solid in order to permit adequate definition of the location of embolism formation. Additionally, the combination of the biocompatible embolizing agent and contrast agent should be compatible and capable of effective placement either by injection or catheter delivery at the vascular site and combinations having too high a viscosity create significant delivery difficulties and possible vascular damage during delivery.

Whether an embolizing agent and contrast agent will be suitable in combination to embolize a blood vessel is very empirical and substitution of one embolizing agent for another or one contrast agent with another often leads to deleterious results. This problem is not particularly surprising because ultimately a successful combination of embolizing agent and contrast agent requires compatibility between these components in producing the requisite coherent precipitate having the contrast agent encapsulated therein as well as maintaining the requisite properties for vascular use. When, for example, one contrast agent is replaced by another contrast agent, the chemical and physical properties of each contrast agent will dictate whether it is compatible with the selected embolizing agent. Accordingly, it is not unexpected that contrast agents having different chemical and/or physical properties will result in changes in the overall properties of the embolizing composition.

Certain compositions comprising an embolizing agent, a contrast agent and a biocompatible solvent such as dimethylsulfoxide (DMSO) have heretofore been disclosed. For example, Mandai, et al.[1] and Kinugasa, et al.[2] disclose an embolizing composition comprising cellulose acetate as the embolizing agent in DMSO employing bismuth trioxide as the contrast agent for catheter delivery to the vascular site. The cellulose acetate employed therein is cellulose triacetate as reported by Naitoh, et al.[3] and the data set forth in the examples below show that embolizing compositions employing cellulose triacetate, at a concentration sufficient to effectively embolize the blood vessel, have too high a viscosity to be readily suitable for vascular delivery. Moreover, the use of bismuth trioxide as the contrast agent is not favored in view of recent evidence indicating that exposure to this agent can lead to progressive mental confusion, irregular myoclonic jerks, a distinctive pattern of disordered gait, and a variable degree of dysarthria which was fatal to patients who continued its use[4].

In view of the above, there is an ongoing need for an embolizing composition having properties particularly suited for vascular delivery.

SUMMARY OF THE INVENTION

This invention is directed to the discovery that the embolizing compositions comprising cellulose diacetate (having an acetyl content of from about 31 to about 40 weight percent) provide for surprising and unexpected properties relative to compositions comprising either cellulose monoacetate or cellulose triacetate as the embolizing agent.

Moreover, this invention is directed to the further discovery that embolizing compositions comprising cellulose diacetate and a contrast agent selected from the group consisting of tantalum, tantalum oxide and barium sulfate provide compatible embolizing/contrast agent combinations.

Accordingly, in one of its composition aspects, this invention is directed to an embolizing composition comprising:

(a) from about 2.5 to about 8.0 weight percent of a cellulose diacetate embolizing agent wherein said cellulose diacetate has an acetyl content of from about 31 to about 40 weight percent;

(b) from about 10 to about 40 weight percent of a water insoluble contrast agent selected from the group consisting of tantalum, tantalum oxide and barium sulfate;

(c) from about 52 to about 87.5 weight percent of a biocompatible solvent wherein the weight percent of the cellulose acetate, water insoluble contrast agent and biocompatible solvent is based on the total weight of the complete composition.

In one of its method aspects, this invention is directed to a method for embolizing a blood vessel by injecting into said blood vessel a sufficient amount of an embolizing composition comprising:

(a) from about 2.5 to about 8.0 weight percent of a cellulose diacetate embolizing agent wherein said cellulose diacetate has an acetyl content of from about 31 to about 40 weight percent;

(b) from about 10 to about 40 weight percent of a water insoluble contrast agent selected from the group consisting of tantalum, tantalum oxide and barium sulfate;

(c) from about 52 to about 87.5 weight percent of a biocompatible solvent wherein the weight percent of the cellulose acetate, water insoluble contrast agent and biocompatible solvent is based on the total weight of the complete composition under conditions wherein a precipitate is formed which embolizes the blood vessel.

In a preferred embodiment, the number average molecular weight of the cellulose diacetate composition is from about 25,000 to about 100,000 more preferably from about 50,000 to about 75,000 and still more preferably from about 58,000 to 64,000. The weight average molecular weight of the cellulose diacetate composition is preferably from about 50,000 to 200,000 and more preferably from about 100,000 to about 180,000.

Preferably, the biocompatible solvent is dimethylsulfoxide.

DETAILED DESCRIPTION OF THE INVENTION

This invention is directed to specific embolizing compositions comprising a specific embolizing agent, specific contrast agents and a biocompatible solvent.

Prior to discussing this invention in further detail, the following terms will first be defined:

The term "embolizing" as used in conjunction with "embolizing compositions" and "embolizing agents" refers to a process wherein a material is injected into a blood vessel which thereafter fills or plugs the blood vessel and/or encourages clot formation so that blood flow through the vessel ceases. The embolization of the blood vessel is important in preventing/controlling bleeding (e.g., organ bleeding, gastrointestinal bleeding, vascular bleeding, bleeding associated with an aneurysm) or to ablate diseased tissue (e.g., tumors, etc.) by cutting off its blood supply.

The term "cellulose diacetate" refers to cellulose polymers composed of at least about 95 weight percent anhydroglucose units which anhydroglucose units are 1→4 beta-linked via an oxygen (ether) linkage to form substantially linear chains and which polymers are characterized as having an acetyl content of from about 31 to about 40 weight percent.

The term "cellulose triacetate" refers to cellulose polymers composed of at least about 95 weight percent anhydroglucose units which anhydroglucose units are 1→4 beta-linked via an oxygen (ether) linkage to form substantially linear chains and which polymers are characterized as having an acetyl content of from above 40 to 44.8 weight percent.

The term "cellulose monoacetate" refers to cellulose polymer composed of at least about 95 weight percent anhydroglucose units which anhydroglucose units are 1→4 beta-linked via an oxygen (ether) linkage to form substantially linear chains and which polymers are characterized as having an acetyl content of from above about 29.0 to less than 31 weight percent.

Methods for determining the acetyl contents of the different cellulose acetates are set forth in National Formulary, *Cellulose/Official Monograms* 18:2232, which is incorporated herein by reference in its entirety.

Cellulose diacetate polymers used herein are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

The term "contrast agent" refers to a radiopaque material capable of being monitored during injection into a mammalian subject by, for example, radiography. The term "water insoluble contrast agent" refers to contrast agents which are essentially insoluble in water (i.e., having a water solubility of less than 0.01 mg/ml at 20° C.). The water insoluble contrast agents included within the scope of this invention are tantalum, tantalum oxide and barium sulfate, each of which is commercially available in the proper form for in vivo use including a particle size of about 10 μm or less. Other contrast agents suitable for use herein include gold and platinum.

The term "biocompatible solvent" refers to an organic material liquid at least at body temperature of the mammal in which the cellulose diacetate is soluble and, in the amounts used, is substantially non-toxic. Suitable biocompatible solvents include, by way of example, dimethylsulfoxide, analogues/homologues of dimethylsulfoxide, ethanol, acetone, and the like. Preferably, the biocompatible solvent is dimethylsulfoxide.

The term "encapsulation" as used relative to the contrast agent being encapsulated in the precipitate is not meant to infer any physical entrapment of the contrast agent within the precipitate much as a capsule encapsulates a medicament. Rather, this term is used to mean that the contrast agent and copolymer form an integral coherent precipitate which does not separate into a copolymer component and a contrast agent component.

Compositions

The compositions of this invention are prepared by conventional methods whereby each of the components is added and the resulting composition mixed together until the overall composition is substantially homogeneous. Specifically, sufficient amounts of the cellulose diacetate polymer are added to the biocompatible solvent to achieve the effective concentration for the complete embolizing composition. Preferably, the embolizing composition will comprise from about 2.5 to about 8.0 weight percent of the cellulose diacetate polymer composition based on the total weight of the embolizing composition and more preferably from about 4 to about 5.2 weight percent. If necessary, gentle heating and stirring can be used to effect dissolution of the copolymer into the biocompatible solvent, e.g., 12 hours at 50 ° C.

Sufficient amounts of the contrast agent are then added to the biocompatible solvent to achieve the effective concentration for the complete embolizing composition. Preferably, the embolizing composition will comprise from about 10 to about 40 weight percent of the contrast agent and more preferably from about 20 to about 40 weight percent and even more preferably 35 weight percent. Insofar as the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Methods

The compositions described above are then employed in methods for embolizing mammalian blood vessels. Specifically, a sufficient amount of this composition is introduced into the selected blood vessel by conventional means (e.g., injection or catheter delivery under fluoroscopy) so that upon precipitation of the cellulose acetate polymer, the blood vessel is embolized. The particular amount of embolizing composition employed is dictated by the total volume of the vasculature to be embolized, the concentration of polymer in the composition, the rate of precipitation (solids formation) of the polymer, etc. Such factors are well within the skill of the art. The rate of precipitation can be controlled by changing the overall hydrophobicity/hydrophilicity of the polymer with faster precipitation rates being achieved by a more hydrophobic polymer composition which, in turn, can be achieved by increasing the acetyl content.

One particularly preferred method for delivering the embolizing compositions of this invention to the selected vascular site is via a small diameter medical catheter. The particular catheter employed is not critical provided that polymeric catheter components are compatible with the embolizing composition (i.e., the catheter components will not readily degrade in the embolizing composition). In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., Teflon™), silicone, etc.

When delivered by catheter, the injection rate dictates, in part, the form of the precipitate at the vascular site. Specifically, low injection rates of approximately 0.05 to 0.3 cc/minute will provide for a precipitate in the form of a kernel or nodule which is particularly beneficial for site specific embolization because the precipitate forms primarily at the point of injection. Contrarily, high injection rates of about 0.1 to 0.5 or more cc/several seconds (e.g., up to 10 seconds) will provide for a filament like mass projecting downstream from the catheter tip which is particularly beneficial for providing the embolizing agent deep into the vascular tree. Such procedures are suitable for embolizing tumor masses, organs and arteriovenous malformations (AVM).

When introduced into the vascular site, the biocompatible solvent diffuses rapidly into the blood and a solid precipitate forms which precipitate is the cellulose diacetate polymer with the contrast agent encapsulated therein. Without being limited to any theory, it is believed that initially, a soft gel to spongy solid precipitate forms upon contact with the blood which precipitate is open and fibrous in structure. This precipitate then restricts blood flow, entrapping red cells thereby causing clot embolization of the blood vessel.

Utility

The compositions described herein are useful in embolizing mammalian blood vessels which, in turn, can be used to prevent/control bleeding (e.g., organ bleeding, gastrointestinal bleeding, vascular bleeding, bleeding associated with an aneurysm) or to ablate diseased tissue (e.g., tumors, etc.). Accordingly, these compositions find use in human and other mammalian subjects requiring embolization of blood vessels.

Additionally, these compositions provide an appropriate vehicle for the delivery of a medicament to the vascular site. Specifically, a suitable medicament, e.g., a chemotherapeutic agent, growth factor agents, anti-inflammatory agents, anti-spasmatic agents, etc. which are compatible with the embolizing composition can be included in this composition in therapeutic levels and delivered directly to the vascular site.

The following examples are set forth to illustrate the claimed invention and are not to be construed as a limitation thereof.

EXAMPLES

Unless otherwise stated, all temperatures are in degrees Celsius. Also, in these examples, unless otherwise defined below, the abbreviations employed have their generally accepted meaning:
cc=cubic centimeter DMSO=dimethylsulfoxide
gm=gram
mm=millimeter
psi=pounds per square inch

EXAMPLE 1

The purpose of this example is to demonstrate the suitability of different cellulose acetate polymers in DMSO as embolizing agents. The tests were conducted by addition of the polymer solution into saline and determining the precipitation parameters. Rapid formation of a coherent precipitate evidences suitability of the copolymer composition as an embolizing agent.

Specifically, three cellulose acetate polymers of varying acetyl contents (i.e., two cellulose diacetates having an acetyl content of 31.6 and, 39.7 weight percent and a single cellulose triacetate having an acetyl content of 43.3 weight percent each available from FMC Corp., Pharmaceutical Division, Philadelphia, Pa., USA) were employed. The cellulose diacetates (Cellulose Acetate NF CA 320-S (~32% acetyl content), Cellulose Acetate NF CA 398-10 (~39.8 acetyl content)) and the cellulose triacetate (Cellulose Acetate NF CA 435-75S (~43.5% acetyl content)) were all obtained from FMC Corp., Pharmaceutical Division, Philadelphia, Pa., USA.

Samples were prepared at 5.2, 6.8 and 8.3 weight % concentration in DMSO (obtained from Aldrich Chemical Company, Milwaukee, Wis., USA as M8180-2, 99+% purity). Dissolution was complete within 24 hours at 52° C.

The samples prepared using cellulose triacetate were of too high a viscosity for effective delivery via a catheter at a concentration sufficient to effectively embolize a blood vessel and there was much difficulty in even filling a syringe for solution delivery. Reduction of cellulose triacetate concentration to less than 2.5 weight percent resulted in diffuse precipitate formation which was unsuitable for vascular embolization. These results indicate that high acetyl content in the cellulose acetate provided cellulose acetate solutions unacceptable for ready delivery via a catheter to the selected vascular site.

Approximately 0.1 to 0.5 mL of each cellulose diacetate solution was added by needle/syringe to a normal saline solution at 37° C. or at room temperature. All samples immediately generated a white mass or string of polymer upon contact with saline. At equal concentrations, solutions of cellulose acetate having a 39.7 weight percent acetyl content provided a whiter, tougher mass than solutions of cellulose acetate having a 31.6 weight percent acetyl content. At a concentration of 5.2%, the solution of cellulose acetate having a 31.6 weight percent acetyl content produced a precipitate which was especially fragile suggesting that about 31 weight percent acetyl content is the effective lower limit for acetyl content in the cellulose acetate. Moreover, cellulose acetate having an acetyl content ofless than 31% is water soluble and, accordingly, is not suitable for use as an embolic agent.

Flow rates were assessed for each of these samples at 10 psi and 37° C. over 3 minutes using a 3 French Infusion catheter (available from Micro Therapeutics, Inc., Aliso Viejo, Calif., USA) in order to assess suitability for catheter delivery of these compositions to the vascular site. The results of this analysis are set forth in Table I below:

TABLE I

| Concentration of Cellulose Acetate Polymer | Flow Rate for Cellulose Acetate having a 31.6 wt % acetyl content | Flow Rate for Cellulose Acetate having a 39.7 wt % acetyl content | Flow Rate for Cellulose Acetate having a 43.3 wt % acetyl content |
| --- | --- | --- | --- |
| 5.2% | 0.23 cc/min | 0.11 cc/min | too viscous to measure |
| 6.8% | 0.12 cc/min | 0.07 cc/min | too viscous to measure |
| 8.3% | 0.06 cc/min | 0.03 cc/min | too viscous to measure |

The above results indicate that cellulose diacetate compositions possess flow rates suitable for catheter delivery to the vascular site but that cellulose triacetate compositions do not. These results also suggest that preferable results are achieved using the more hydrophobic cellulose diacetate composition (e.g., about 39.7 weight percent acetyl content) at a concentration of about 5 to about 7 weight percent relative only to the biocompatible solvent.

In view of the above, cellulose acetates having an acetyl content of from about 31 to about 40 weight percent are suitable for use in embolization composition.

It is contemplated that other cellulose acetates such as cellulose acetate butyrate, cellulose acetate proprionate, etc. will also be useful in the embolization compositions.

EXAMPLE 2

The purpose of this example is to illustrate that not all polymers are suitable as embolizing agents. Specifically, in this example, the cellulose diacetate polymers described above were replaced with polyurethane (Dow PELLETHANE 2363-80A, Dow Chemical Company, Midland, Mich., USA), polymethylmethacrylate (available from Rohm & Haas, Philadelphia, Pa., USA), polycarbonate (MOBAY MAKROLON 2558-1112, Bayer Inc., Pittsburgh, Pa., USA), ethylene vinyl alcohol copolymers (EVAL Company of America, Lisle, Ill., USA).

The results of this analysis indicated that polyurethane samples were slow to dissolve in DMSO at 52° C. and, upon cooling to room temperature, formed a high viscosity solution/gel unsuitable for injection. In the case of the polymethylmethacrylate, the polymer dissolved in DMSO but the precipitate formed upon addition to saline was unsuitable for use as an embolizing agent because it lacked cohesiveness and easily fragmented. In the case of the polycarbonate, the polymer failed to dissolve in DMSO at 52° C. over 3 days. Only the ethylene vinyl alcohol copolymers provided suitability for vascular embolization in a manner similar to EVOH and the use of such polymers as embolizing agents is described in further detail in U.S. patent application Ser. No. 08/507,863 filed concurrently herewith as Attorney Docket No. 018413-002 entitled "NOVEL COMPOSITIONS FOR USE IN EMBOLIZING BLOOD VESSELS" which application is incorporated herein by reference in its entirety.

EXAMPLE 3

The purpose of this example is to compare in vitro results achieved by incorporating a water soluble contrast agent and a water insoluble contrast agent of this invention into an embolizing composition containing cellulose acetate in DMSO. Specifically, in this example, cellulose diacetate (39.7 weight percent acetyl content) was dissolved into DMSO to provide for an 6.8 weight percent concentration of the copolymer in DMSO. To this solution was added either tantalum (10 weight percent, available from Leico Industries, New York, N.Y., USA, 99.95% purity, less than 43 μm in size) or metrizamide (38.5 weight percent, available from Aldrich Chemical Company, Milwaukee, Wis., USA) as a water soluble contrast agent. Because these results are in vitro results, the tantalum particle size is not important and the larger particles size is not expected to affect these results.

In the tantalum composition, tantalum settling can result from prolonged standing. Sonification may help but throrough mixing prior to use is required.

Approximately 0.2 mL of the each composition was then added by syringe/needle to a saline solution at 37° C. and the characteristics of the resulting precipitate examined. In the case of the tantalum sample, a precipitate immediately formed which was characterized by firm spongy filaments and nodules. The metrizamide sample on the other hand did not form a well defined solid mass as the metrizamide rapidly diffused away.

Bismuth trioxide gave similar results to tantalum but is deemed not to be a biocompatible contrast agent because recent evidence indicates that exposure to this agent can lead to progressive mental confusion, irregular myoclonic jerks, a distinctive pattern of disordered gait, and a variable degree of dysartkria which was fatal to patients who continued its use[4].

From the foregoing description, various modifications and changes in the composition and method will occur to those skilled in the art. All such modifications coming within the scope of the appended claims are intended to be included therein.

What is claimed is:

1. A composition comprising:
   (a) from about 2.5 to about 8 weight percent of a cellulose diacetate having an acetyl content of from about 31 to about 40 weight percent;
   (b) from about 10 to about 40 weight percent of a water insoluble contrast agent selected from the group consisting of tantalum, tantalum oxide and barium sulfate;
   (c) from about 52 to about 87.5 weight percent of a biocompatible solvent
   wherein the weight percent of the cellulose diacetate, water insoluble contrast agent and biocompatible solvent is based on the total weight of the complete composition.

2. The composition according to claim 1 wherein said cellulose diacetate comprises about 39.8 weight percent acetyl content.

3. The composition according to claim 2 wherein said biocompatible solvent is DMSO.

4. The composition according to claim 3 wherein said contrast agent is tantalum.

5. The composition according to claim 3 wherein said contrast agent is tantalum oxide.

6. The composition according to claim 3 wherein said contrast agent is barium sulfate.

7. A method for embolizing a blood vessel by injecting into said blood vessel a sufficient amount of an embolizing composition comprising:
   (a) from about 2.5 to about 8 weight percent of a cellulose diacetate embolizing agent wherein said cellulose diacetate has an acetyl content of from about 31 to about 40 weight percent;
   (b) from about 10 to about 40 weight percent of a water insoluble contrast agent selected from the group consisting of tantalum, tantalum oxide and barium sulfate;
   (c) from about 52 to about 87.5 weight percent of a biocompatible solvent
   wherein the weight percent of the cellulose acetate, water insoluble contrast agent and biocompatible solvent is based on the total weight of the complete composition
   under conditions wherein a precipitate is formed which embolizes the blood vessel.

8. The method according to claim 7 wherein said cellulose diacetate polymer comprises about 39.8 weight percent acetyl content.

9. The method according to claim 8 wherein said biocompatible solvent is DMSO.

10. The method according to claim 9 wherein said contrast agent is tantalum.

11. The method according to claim 9 wherein said contrast agent is tantalum oxide.

12. The method according to claim 9 wherein said contrast agent is barium sulfate.

13. The method according to claim 7 wherein the embolizing composition is injected into the blood vessel at a rate of about 0.05 to 0.3 cc/minute.

14. The method according to claim 7 wherein the embolizing composition is injected into the blood vessel at a rate of at least 0.6 cc/minute.

15. The method according to claim 14 wherein the injection rate of at least 0.6 cc/minute is employed to form a filament like mass projecting down stream from the catheter tip for embolizing tumor masses, organs and arteriovenous malformations (AVM).

* * * * *